(12) United States Patent
Asgeirsson

(10) Patent No.: US 8,940,057 B2
(45) Date of Patent: Jan. 27, 2015

(54) CASTING LINER, AND METHOD AND KIT FOR USING THE SAME

(75) Inventor: Sigurdur Asgeirsson, Gardabaer (IS)

(73) Assignee: Ossur HF, Reykjavik (IS)

(*) Notice: Subject to any disclaimer, the term of this patent is extended or adjusted under 35 U.S.C. 154(b) by 38 days.

(21) Appl. No.: 13/347,133

(22) Filed: Jan. 10, 2012

(65) Prior Publication Data

US 2012/0185060 A1    Jul. 19, 2012

Related U.S. Application Data

(60) Provisional application No. 61/432,277, filed on Jan. 13, 2011.

(51) Int. Cl.
*A61F 2/80* (2006.01)
*A61F 2/78* (2006.01)

(52) U.S. Cl.
CPC ........ *A61F 2/7812* (2013.01); *A61F 2/80* (2013.01)
USPC ............................................................ 623/36

(58) Field of Classification Search
USPC ............................................................ 623/36
See application file for complete search history.

(56) References Cited

U.S. PATENT DOCUMENTS

| | | |
|---|---|---|
| 5,503,543 A | 4/1996 | Laghi |
| 5,718,925 A | 2/1998 | Kristinsson et al. |
| 5,885,509 A | 3/1999 | Kristinsson |
| 5,971,729 A | 10/1999 | Kristinsson et al. |
| 5,972,036 A | 10/1999 | Kristinsson et al. |
| 6,136,039 A | 10/2000 | Kristinsson et al. |
| 6,416,703 B1 | 7/2002 | Kristinsson et al. |
| 6,485,776 B2 | 11/2002 | Janusson et al. |
| 6,626,952 B2 | 9/2003 | Janusson et al. |
| 6,706,364 B2 | 3/2004 | Janusson et al. |
| 6,991,444 B1 | 1/2006 | Laghi |
| 7,001,563 B2 | 2/2006 | Janusson et al. |
| 7,025,793 B2 | 4/2006 | Egilsson |
| 7,105,122 B2 | 9/2006 | Karason |
| 7,118,602 B2 | 10/2006 | Bjarnason |
| 7,169,189 B2 | 1/2007 | Bjarnason et al. |
| 7,438,843 B2 | 10/2008 | Asgeirsson |
| 2007/0123998 A1 | 5/2007 | Egilsson et al. |
| 2010/0249949 A1 | 9/2010 | Bjarnason et al. |
| 2011/0208321 A1* | 8/2011 | Doddroe et al. ............... 623/36 |

* cited by examiner

*Primary Examiner* — Bruce E Snow
(74) *Attorney, Agent, or Firm* — Workman Nydegger

(57) ABSTRACT

A tubular casting liner for forming a definitive prosthetic socket includes an outer layer defining first and second surfaces and at least one polymeric layer having first and second surfaces. The first outer layer surface continuously defines at least a portion of the exterior surface of the casting liner, and the at least one polymeric layer first surface is secured to the second surface of the outer layer. A ratio of thickness of the at least one polymeric layer at the distal end area relative to the proximal end area is at least 3:1. The casting liner has a substantially straight profile, wherein a diameter d1 of the liner whereat the distal end area begins to transition to close-ended form is the same or substantially the same as a diameter d2 at the proximal end area. A method and kit for forming a definitive prosthetic socket may use the casting liner.

16 Claims, 2 Drawing Sheets

CASTING LINER, AND METHOD AND KIT FOR USING THE SAME

CROSS-REFERENCE TO RELATED APPLICATIONS

This application claims the benefit of priority from U.S. Provisional Application No. 61/432,277, filed on Jan. 13, 2011, the entirety of which is incorporated herein by reference.

BACKGROUND

Definitive sockets for fitting prostheses to residual limbs of amputees are made by various processes in accordance with prior art techniques. For example, numerous techniques have been developed that involve first, creating a negative mold of the residual limb, second, creating a positive mold or impression cast from the negative mold, third, modifying the positive mold to provide relief for sensitive areas of the residual limb, and fourth, forming the prosthesis socket using the modified positive mold. This technique involves numerous steps, and the negative and positive molds are typically created using Plaster-of-Paris. Some examples of this technique are embodied in U.S. Pat. No. 5,503,543, granted Apr. 2, 1996; and U.S. Pat. No. 6,991,444 granted Jan. 31, 2006, both to Laghi.

Another technique used to form prosthetic sockets is to reduce the steps in the above process by forming the socket directly on the residual limb without creating both a negative and a positive mold. This technique can be implemented in a variety of ways.

For example, U.S. Pat. No. 5,718,925, granted Feb. 15, 1998; U.S. Pat. No. 5,971,729, granted Oct. 26, 1999; U.S. Pat. No. 5,972,036, granted Oct. 26, 1999; and U.S. Pat. No. 6,416,703 granted Jul. 9, 2002, all to Kristinsson et al., and all herein incorporated by reference, all disclose a method of forming a definitive prostheses socket directly upon a residual limb. In the method, a web-like tubular braided carbon fiber sleeve that is pre-impregnated with a water curable resin is soaked in water and placed upon the residual limb. The sleeve is pressure cast in a known manner using the ICECAST ANATOMY™ system made by Össur hf of Reykjavik, Iceland, and described in U.S. Pat. No. 5,885,509, granted Mar. 23, 1999 to Kristinsson, and further modified by U.S. Pat. No. 7,105,122, granted on Sep. 12, 2006 to Karason, and U.S. Pat. No. 7,438,843, granted Oct. 21, 2008 to Asgeirsson, each of these references being herein incorporated by reference in their entirety.

U.S. Pat. No. 7,438,843 discloses another method and kit for forming a prosthetic socket directly on a residual limb. The method and kit are used to form a definitive prosthetic socket directly on a residual limb without the use of a water hardenable material. A chamber surrounding a web of braided fibers is created on the residual limb via the use of inner and outer protective sheaths. A hardenable or curable material for forming the prosthetic socket is injected into the chamber around the web. Pressure is applied around the chamber to form the definitive prosthetic socket. The same basic method may be used likewise with a positive impression cast of the residual limb.

An issue arises when forming sockets due to the residual limb deforming during the casting process. As such, the profile of the residual limb varies during casting over the normal state of the residual limb. This results in a socket that has a poor fit with the residual limb leading to painful pressure on the residual limb due to pressure points. From this poor fit, the residual limb runs the risk of forming blisters, sores and decreased blood flow.

When creating a socket, it is desired to obtain total surface bearing due to a volume match of the socket to the residual limb. If the residual limb reduces in volume, it will further drop into the socket resulting in increased distal pressure on the residual limb. If the residual limb increases in volume, it cannot fit properly into the socket, resulting in discomfort over bony prominences and excessive tension at the distal end of the residual limb.

It follows that there should be as close as possible full surface contact between the socket and the residual limb during a normal walking gait cycle. Thus, in order to successfully fit a socket to a residual limb, there must be control of the soft tissue, a minimization of pressure peaks, and a distribution of the load on the residual limb over a maximum surface area.

In many conventional casting methods, a standard suspension liner is donned on the residual limb to approximate the necessary volume of the residual limb and suspension liner. Yet, the standard suspension liner often creates too much volume for the socket and thereby leads to a poorly fitting socket. This necessitates for manual manipulation of the socket to achieve the necessary volume, and therefore adds to manufacturing time and requires substantial skill to achieve the necessary volume.

In order to assure that there is total surface bearing between the residual limb and the socket, a method and kit for casting a socket must evenly distribute the soft tissue, minimize modifications of the socket, and provide consistent results. In particular, it is undesirable to modify the cast, such as Plaster-of-Paris, for volume reduction of the socket, or manually modify a socket that has been directly cast on a residual limb. Regrettably, many of the known methods and kits for forming sockets fail to achieve these desired results.

SUMMARY

The casting liner, and kit and method for forming a prosthetic socket using the casting liner overcome a number of disadvantages present in the prior art, such as removing the need to modify a cast or socket for volume reduction, due in part to its inherent shape and thickness. Usage of the casting liner allows for an improved fit between the socket and the residual limb over known kits and methods used to form sockets. This is obtained by limiting or preventing deformation of the residual limb during a direct casting process, and yields a socket with more predictable shape and hence results without necessitating as much skill and experience of the prosthetist and increasing manufacturing time.

In accordance with an embodiment of the casting liner, the tubular casting liner includes an outer layer defining first and second surfaces and at least one polymeric layer having first and second surfaces. The first outer layer surface continuously defines at least a portion of the exterior surface of the casting liner, and the at least one polymeric layer first surface is secured to the second surface of the outer layer.

A ratio of thickness of the at least one polymeric layer at the distal end area relative to the proximal end area may be at least 3:1. The casting liner may have a substantially straight profile such that a diameter d1 of the liner whereat the distal end area of the liner begins to transition to close-ended form is the same or substantially the same as the diameter d2 at the proximal end area. The thickness of the at least one polymeric layer may continuously taper from the distal end area to the proximal end area.

The casting liner defines a mid-section area located between the proximal and distal end areas such that a ratio of thickness of the at least one polymeric layer at the mid-section area relative to the distal end area is 2:1. The casting liner may have a concave curved connector located at the distal end area of the casting liner. In a variation, the connector is substantially more rigid than the at least one polymeric layer. The casting liner may have a distal cap extending over the connector and forming the exterior surface of the casting liner at the distal end. The distal cap and the outer layer may form the entirety of the exterior surface of the casting liner.

According to an embodiment, the outer layer forms an elasticity controlling matrix material that is compliant in a radial direction and substantially rigid or inelastic in an axial direction of the casting liner. The elasticity controlling matrix material may be located within the at least one polymeric layer, and the matrix material may be compliant in a radial direction and substantially rigid or inelastic in an axial direction of the casting liner.

In another embodiment, the at least one polymeric layer may include a first continuous polymeric layer having first and second surfaces in which the first polymeric layer first surface is bonded to the interior surface of the outer layer. A second continuous polymeric layer has first and second surfaces such that the second first layer surface is contiguous and integrally secured to the first layer second surface. The second polymeric layer is preferably thicker than the first polymeric layer, and the second layer surface forms the interior surface as a continuously smooth surface.

According to a variation, the second polymeric layer may have hardness substantially less than hardness of the first polymeric layer. The first polymeric layer may have a thickness substantially less than a thickness pertaining to the second polymeric layer. The second polymeric layer is preferably but not limited to a silicone elastomer.

A method for forming a rigid prosthetic socket corresponding to a residual limb includes the use of the casting liner. The method involves placing a casting liner over a residual limb or cast representing the residual limb, and controlling volume reduction of the prosthetic socket at a proximal end area by a reduction of thickness of the casting liner at the proximal end area relative to the distal end area. The casting liner may involve any of the features described above.

The method may further involve the steps of placing a web over the casting liner, placing an outer protective sheath over the web, forming a first seal at a proximal end between the casting liner and the outer protective sheath, and forming a second seal at a distal end between the casting liner and the outer protective sheath. From this method, an enclosed zone is formed around the web between the casting liner and the outer protective sheath, and material is injected into the enclosed zone to form the prosthetic socket.

A kit for forming a definitive prosthetic socket may use the casting liner having any of the features described above as well as employ any of the aforementioned method steps.

The numerous advantages, features and functions of the various embodiments of the casting liner, and method and kit for using the same, will become readily apparent and better understood in view of the following description and accompanying drawings. The following description is not intended to limit the scope of the casting liner, but instead merely provides exemplary embodiments for ease of understanding.

Figure 1:
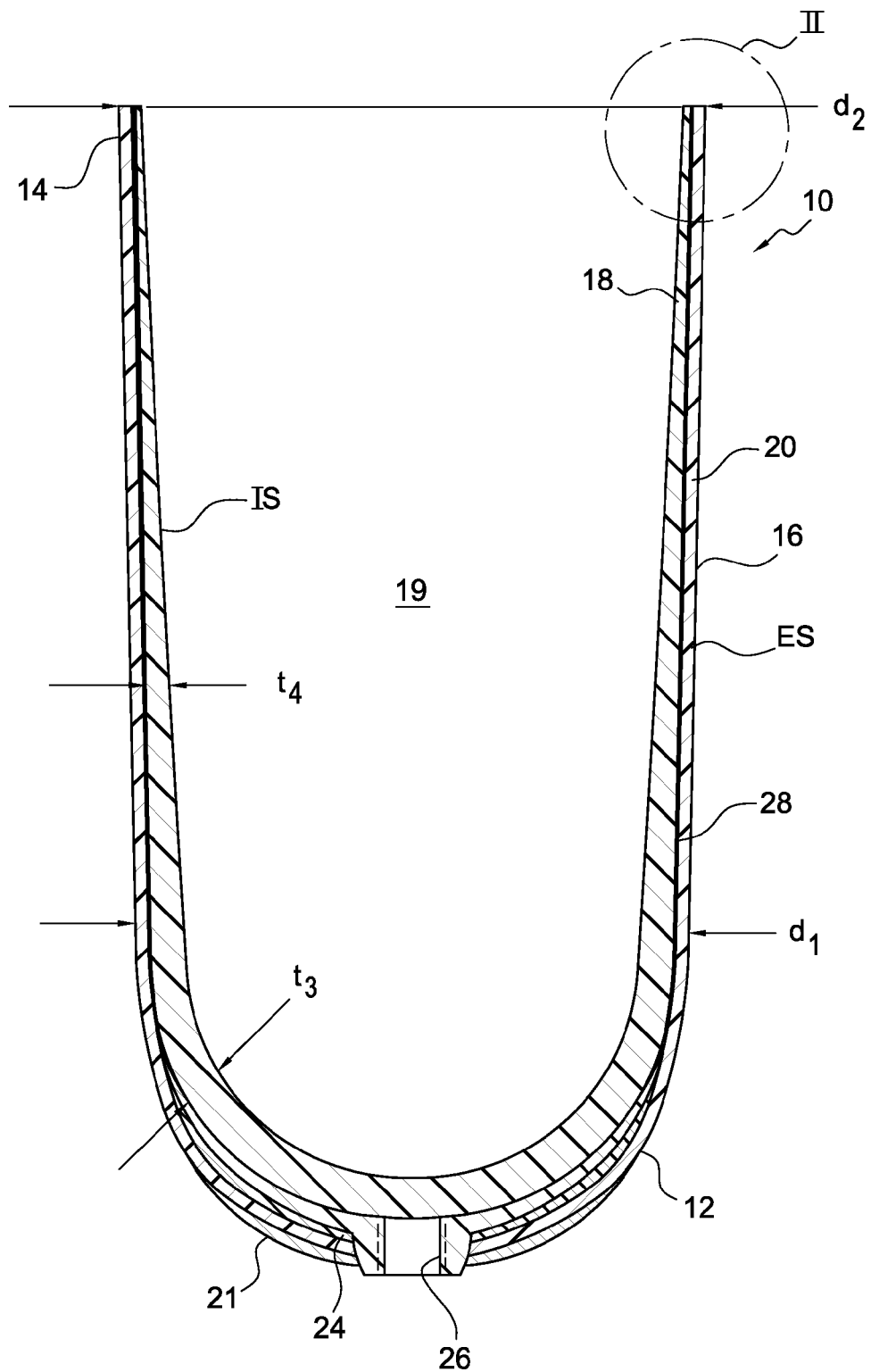
FIG. 1 is an elevational cross-sectional view illustrating an embodiment of the casting liner.

In the various figures, similar elements are provided with similar reference numbers. It should be noted that the drawing figures are not necessarily drawn to scale, or proportion, but instead are drawn to provide a better understanding of the components thereof, and are not intended to be limiting in scope, but rather provide exemplary illustrations.

DETAILED DESCRIPTION OF VARIOUS EMBODIMENTS

The embodiments described herein are for a casting liner, which forms an interface between a positive impression cast representing a residual limb and socket components during an indirect or standard lamination of a rigid or semi-rigid socket, or between the skin of a residual limb and socket components for forming a socket while the socket is formed over the residual limb during a direct casting process. The casting liner stabilizes soft tissue of the residual limb by preventing the cast or residual limb from deforming when casting the socket. The casting liner also eliminates the necessity for reducing volume of the socket, due in part to its inherent shape and thickness, thereby leading to sockets that have a more predictable shape and minimize undesirable pressure points.

In an embodiment of the liner, FIG. 1 schematically illustrates in a cross-section view a prosthetic liner 10 arranged as a tubular liner adapted to envelop a residual limb. The liner is air and moisture impervious, and has an open proximal end arranged to permit entry of the residual limb into an interior cavity 19 formed by the liner. The cavity is defined by a continuous interior surface IS and a closed-end distal end area such that the cavity is arranged to receive and closely envelop residual limb. The liner defines an exterior surface ES which generally conforms to the residual limb.

The casting liner 10 includes a distal end area 12, a proximal end area 14, and an axially extending mid-section 16, located between the distal and proximal end areas 12, 14. When donned on either a cast of a residual limb or a residual limb itself, the casting liner is air-tight.

The liner 10 is formed in part by an outer layer 20, such as an elasticized fabric layer, along its exterior surface ES, an intermediate, first polymeric layer 18, such as silicone elastomer, and a second polymeric layer 28, such as silicone elastomer, formed along the interior surface IS. The entire assembly of the outer layer, the first polymeric layer, and the second polymeric layer is at least freely radially elastically distendable.

The outer layer 20 defines outer and inner surfaces whereby the outer surface continuously forms the exterior surface ES of the liner 10 through the proximal end area 14 as well as the mid-section area 16. The second polymeric layer 28 has inner and outer surfaces, and the outer surface is intimately and continuously bonded to the inner surface of the outer layer 20. The first polymeric layer 18 has inner and outer surfaces wherein the outer surface of the second polymeric layer 28 is contiguous and integrally secured to the inner surface of the first polymeric layer 18.

The inner surface of the first polymeric layer 18 defines the inner surface IS of the liner 10. The inner surface of the first polymeric layer 18 is continuously smooth meaning that it is without interruption and does not form any substantial recesses or protrusions, as shown in FIG. 1. The smooth surface allows for pressure relief and comfortably accommodates bony prominences, sensitive areas and scarred tissue of the residual limb.

Figure 2:
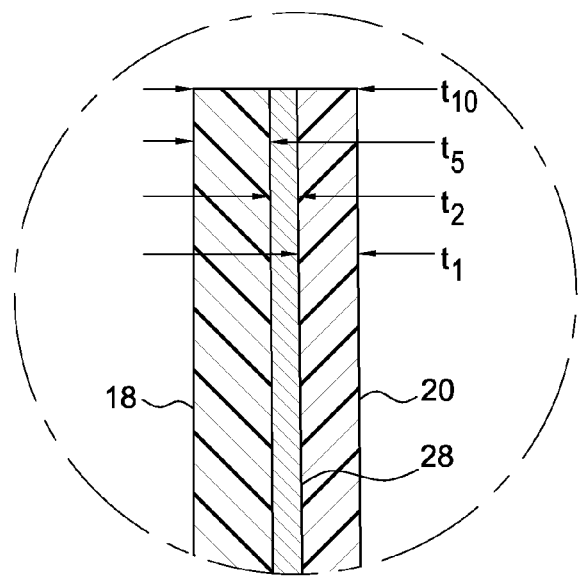
FIG. 2 is a detail view of section II located at a proximal end area of the casting liner of FIG. 1.

As shown in FIGS. 1 and 2, the first polymeric layer 18 tapers in thickness from a relatively thick cross-section at the distal end area 12 of the liner to a substantially thinner cross-section at the proximal end area 14 of the liner. The outer layer 20 has a generally uniform thickness across the distal end area 12, the mid-section area 16, and the proximal end area 14. The second polymeric layer 28 likewise has a generally uniform thickness across the distal end area 12, the mid-section 16, and the proximal end area 14. The liner has a substantially straight configuration although thickness of the first polymeric layer varies and substantially diminishes towards the proximal end area 14.

The outer layer is normally air permeable and may be formed from a flat knit elasticized fabric. The inner surface of the outer layer is coated with the second polymeric layer 28 defined as a thin layer of cured silicone elastomer preferably partially embedded in the fibers of the textile without completely penetrating the textile. The outer layer is preferably seamless along the sides of the liner.

The first polymeric layer is preferably a silicone elastomer that has hardness properties lower than hardness properties of the first polymeric layer. Moreover, the first polymeric layer preferably has a thickness greater than a thickness of the second polymeric layer. The first polymeric layer may include hollow thermoplastic microspheres, silicone oil, and/or one or more skin treatment agents.

The outer layer, and the first and second polymeric layers may be formed in accordance with any of the following U.S. Pat. Nos. 6,136,039, 6,626,952, 6,485,776, 6,706,364, 7,001,563 and 7,118,602, each of which are incorporated herein by reference in their entirety. The liner embodiments of the pending application may be configured to include any of the features of the aforementioned patents In accordance with the embodiment of FIGS. 1 and 2, a reinforcement matrix formed from an elasticity controlling material is incorporated into the outer layer 20. The elasticity controlling material is compliant in the radial direction and substantially rigid or inelastic in the axial direction. The elasticity controlling properties of the outer layer prevents the residual limb from deforming during the casting process of a socket, and thereby allows for substantially uniform redistribution of pressure so as to minimize the formation of any possible pressure points in the definitive socket.

Figure 3:
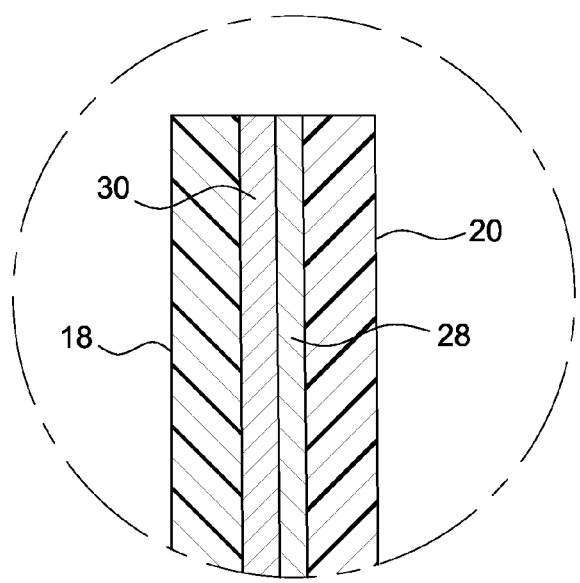
FIG. 3 is a detail view of an alternative to section II depicted in FIG. 2.

As depicted in FIG. 3, an alternative embodiment of the liner 10 may include a distension controlling reinforcement matrix 30 located along the interface between the first and second polymeric layers 18, 28, and extend over the entire length of the liner. In this embodiment, the outer layer 20 is a textile material, such as nylon, with the reinforcement matrix controlling the axial extension of the liner so as to eliminate longitudinal stretching of soft tissue of the residual limb.

In any of the embodiments, the reinforcement matrix may contain reinforcement elements that provide substantial stiffness against elongation of the liner in a direction along the liner length. The reinforcement elements may comprise interlocked fibers such as a circular knit tubular fabric that strongly resist longitudinal elongation but readily distends radially. An example of a reinforcement matrix is described by U.S. Pat. No. 6,706,364.

The liner of FIG. 1 includes a connector 24 having a concave curved configuration, and a threaded opening 26. The connector 24 is embedded into the first polymeric layer 18. A distal end cap 21 is formed or bonded to the distal end of the liner, and surrounds threaded opening 26. The shape of the umbrella connector is not limited to the variation shown herein and may also correspond to the umbrella connector in combination with a distal end cap as taught in U.S. Pat. No. 6,485,776.

In reference to FIGS. 1 and 2, the casting liner has a substantially straight profile, wherein the diameter of the liner at d1 whereat the liner begins to transition to close-ended form is the same or substantially the same as d2 at the proximal end area 14 of the liner. The thickness $t_1$ of the outer layer 20 is substantially if not the same along the entirety of the liner 10, as is the thickness $t_2$ of the second polymeric layer 28.

The thickness of the first polymeric layer 18 gradually tapers from the distal end area of the liner to the proximal end area of the liner. For example, a thickness $t_3$ at the distal end area 12 is substantially greater than the thickness $t_4$ at the mid-section 16, and the thickness $t_4$ is substantially greater than the thickness $t_5$ at the proximal end area 14. For example, the thickness ratio of $t_3$ to $t_5$ is at least 1:4, whereas the thickness ratio of $t_4$ to $t_5$ is at least 1:2.

Figure 4:
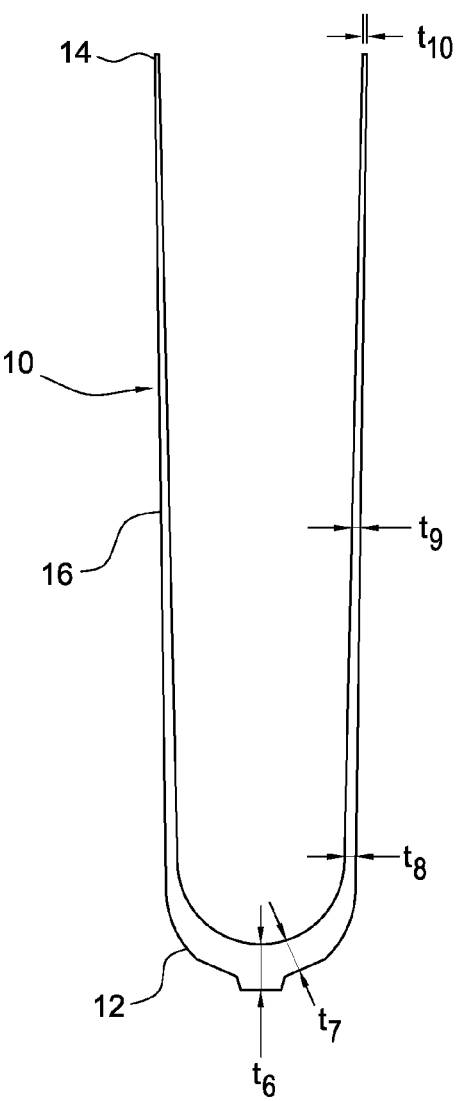
FIG. 4 is another elevational cross-sectional view illustrating the variation in thickness of the first polymeric layer in the casting liner of FIG. 1.

As illustrated in FIG. 4, the casting liner 10 may have the following thicknesses at various locations of the liner. Particularly, at the distal end of the liner excluding the connector the thickness $t_6$ is about 14.25 mm, whereas outside the thickness t6, the thickness $t_7$ is about 14.15 mm. As the liner extends toward the proximal end area 14 from the distal end area 12, the liner has a thickness $t_8$ of about 5 mm. At the mid-section of the liner, the liner has a thickness $t_9$ about 2 mm, whereas at the proximal end area 14, the thickness $t_{10}$ is about 1 mm, in large part due to the reduction in thickness of the first polymeric layer 18.

The severity of the reduction in thickness of the first polymeric layer 18 is in contrast to standard liners used for normal wear with a socket outside of casting the socket. The standard liners typically have a proximal end area thickness of at least 2.5 mm. The substantially thin proximal end area thickness of the casting liners described herein renders the casting liner unsuitable for normal wear with a socket. An example of a standard liner having substantially greater relative thicknesses to the casting liner is found in U.S. Pat. No. 6,136,039.

The casting liner is preferably, but not limited, for use in the method and kit described by U.S. Pat. No. 7,438,843, as well as with the direct casting device described in U.S. Pat. No. 7,105,122. While both of these patents are incorporated by reference, the method and kit in accordance with using the casting liners of this disclosure varies from the aforementioned method and kit.

Specifically, the method for forming a prosthetic socket directly on a residual limb includes the step of first placing the casting liner over the residual limb. This step is different from known methods in that the casting liner replaces either an inner protective sheath or standard suspension liners that are intimately secured the residual limb or cast before casting occurs. The method follows by placing a web over the casting liner, the web including a plurality of fibers capable of receiving a hardenable material; placing an outer protective sheath over the web; forming a first seal at a proximal end between the casting liner and outer protective sheath; forming a second seal at a distal end between the inner and outer protective sheaths so as to form an enclosed zone around the web between the inner and outer protective sheaths; and injecting material into the enclosed zone to form the prosthetic socket.

The method may also include the step of placing an inner protective sheath over the casting liner. The method may also include the step of placing a prosthesis coupler element on the web prior to placing the web over the inner protective sheath.

The prosthesis coupler may be tightened to the casting liner prior to placing the outer protective sheath over the web.

An injection fitting may be placed on the prosthesis coupler element prior to injecting material into the enclosed zone. It is desirable that pressure is applied around the outer protective sheath, after injecting material into the enclosed zone.

After the hardenable material has hardened, the outer protective sheath is removed from around the formed prosthetic socket, and the prosthetic socket is removed from around the inner protective sheath as well as excess material is trimmed from the prosthetic socket.

A kit may be provided to form a socket, and such kit may include the casting liner, an outer protective sheath; a web having a plurality of fibers capable of receiving a hardenable material; and a hardenable material for impregnating the plurality of fibers of the web.

Any of the liner embodiments described herein may be adapted to accommodate a plurality of undulations formed along portions of the liner in accordance with the description of U.S. Pat. Nos. 7,169,189 and 7,118,602, incorporated herein in their entirety by reference. Also, the liner embodiments may be configured to include a seal or seals described in U.S. Pat. No. 7,025,793, and U.S. patent application publication 2007/0123998, incorporated herein in their entirety by reference.

It will be understood that the aforementioned embodiments are not limited to the described liner described herein. Instead, the features of one of the preferred embodiments of this disclosure may readily be combined with those of another or other embodiments of the present disclosure without departing from the scope of the present invention.

It will be readily understood that the described embodiments of the disclosure are exemplary only and various other features and details could be incorporated in the liner described herein without departing from the spirit and scope of the invention as defined in the appended claims. Further, while the liner has been described in connection to a prosthetic liner, the embodiments may be adapted for any suitable prosthetic or orthopedic uses.

The invention claimed is:

1. A tubular casting liner having an open proximal end area and a closed-end distal area, and interior and exterior surfaces, the casting liner forming a cavity delimited by the interior surface, the casting liner adapted to envelop a residual limb, comprising;
   an outer layer defining first and second surfaces, the first outer layer surface continuously defining at least a portion of the exterior surface of the casting liner, the outer layer having a generally uniform thickness;
   at least one polymeric layer having first and second surfaces, the at least one polymeric layer first surface secured to the second surface of the outer layer;
   wherein the ratio of thickness of the at least one polymeric layer at the distal end area relative to the proximal end area is at least 3:1;
   wherein the thickness of the at least one polymeric layer at the distal end area has a dimension, and the at least one polymeric layer having a thickness above the distal end area with dimensions tapering gradually toward the proximal end area;
   wherein the outer layer is an elasticized fabric forming an elasticity controlling matrix material that is compliant in a radial direction and substantially rigid or inelastic in an axial direction of the casting liner, an exterior surface outside of the distal end of the liner consists the elasticized fabric;
   wherein the proximal end area of the liner including the outer layer and the at least one polymeric layer has a thickness of about 1 mm.

2. The casting liner according to claim 1, wherein the casting liner defines a mid-section area located between the proximal and distal end areas, the ratio of thickness of the at least one polymeric layer at the mid-section area relative to the distal end area is 2:1.

3. The casting liner according to claim 1, further comprising a concave curved connector located at the distal end area of the casting liner, the connector being substantially more rigid than the at least one polymeric layer.

4. The casting liner according to claim 1, further comprising a distal cap extending over the connector and forming the exterior surface of the casting liner at the distal end, wherein the distal cap and the outer layer form the entirety of the exterior surface of the casting liner.

5. The casting liner according to claim 1, wherein the casting liner has a substantially straight profile, wherein a diameter d1 of the liner whereat the distal end area begins to transition to close-ended form is the same or substantially the same as a diameter d2 at the proximal end area.

6. The casting liner according to claim 1, further comprising an elasticity controlling matrix material located within the at least one polymeric layer, the matrix material being compliant in a radial direction and substantially rigid or inelastic in an axial direction of the casting liner.

7. The casting liner according to claim 1, wherein the at least one polymeric layer includes:
   a first continuous polymeric layer having first and second surfaces, the first polymeric layer first surface bonded to the interior surface of the outer layer, wherein the first polymeric layer has a thickness less than the outer layer; and
   a second continuous polymeric layer having first and second surfaces, the second first layer surface being contiguous and integrally secured to the first layer second surface, the second polymeric layer being thicker than the first polymeric layer, the second layer surface forming the interior surface as a continuously smooth surface.

8. The casting liner according to claim 7, wherein the second polymeric layer has hardness substantially less than hardness of the first polymeric layer.

9. The casting liner according to claim 7, wherein the first polymeric layer has a thickness substantially less than a thickness pertaining to the second polymeric layer.

10. The casting liner according to claim 7, wherein the second polymeric layer is a silicone elastomer.

11. The casting liner according to claim 1, wherein the thickness of the at least one polymeric layer continuously tapers from the distal end area to the proximal end area.

12. A tubular casting liner having an open proximal end area and a closed-end distal area, and interior and exterior surfaces, the casting liner forming a cavity delimited by the interior surface, the casting liner adapted to envelop a residual limb, comprising;
   an outer layer defining first and second surfaces and consisting an elasticized fabric defining an elasticity controlling matrix, the first outer layer surface continuously defining at least a portion of the exterior surface of the casting liner;
   at least one polymeric layer having first and second surfaces, the at least one polymeric layer first surface secured to the second surface of the outer layer;
   wherein the casting liner has a substantially straight profile, wherein a diameter d1 of the liner whereat the distal end area begins to transition to close-ended form is the same or substantially the same as a diameter d2 at the proximal end area;

wherein the casting liner defines a mid-section area located between the proximal and distal end areas, the ratio of thickness of the at least one polymeric layer at the mid-section area relative to the proximal end area is 2:1;

wherein the proximal end area of the liner including the outer layer and the at least one polymeric layer has a thickness of about 1 mm.

13. The casting layer according to claim 12, wherein the thickness of the at least one polymeric layer at the distal end area has a dimension, and the at least one polymeric layer having a thickness above the distal end area with dimensions tapering gradually toward the proximal end area.

14. A tubular casting liner having an open proximal end area and a closed-end distal area, and interior and exterior surfaces, the casting liner forming a cavity delimited by the interior surface, the casting liner adapted to envelop a residual limb, comprising;

an outer layer defining first and second surfaces, the first outer layer surface continuously defining at least a portion of the exterior surface of the casting liner, the outer layer consisting an elasticized fabric defining an elasticity controlling matrix material compliant in a radial direction and substantially rigid or inelastic in an axial direction of the casting liner;

a first continuous polymeric layer having first and second surfaces, the first polymeric layer first surface bonded to the second surface of the outer layer defining an interior surface, the first polymeric layer having a thickness less than the outer layer, the first polymeric layer and the outer layer having a uniform thickness; and a second continuous polymeric layer having first and second surfaces, the second first layer surface being contiguous and integrally secured to the first layer second surface, the second polymeric layer being thicker than the first polymeric layer, the second layer surface forming the interior surface as a continuously smooth surface wherein the ratio of thickness of the second polymeric layer at the distal end area relative to the proximal end area is at least 3:1;

wherein the proximal end area of the liner including the outer layer and the at least one polymeric layer has a thickness of about 1 mm.

15. The casting layer according to claim 14, wherein the thickness of the at least one polymeric layer at the distal end area has a dimension, and the at least one polymeric layer having a thickness above the distal end area with dimensions tapering gradually toward the proximal end area.

16. The casting layer according to claim 14, wherein the first polymeric layer is at least partially embedded in fibers of the elasticized fabric without completely penetrating the fabric.

\* \* \* \* \*